United States Patent
Harada et al.

(10) Patent No.: US 8,876,840 B2
(45) Date of Patent: Nov. 4, 2014

(54) MEDICAL SUTURING TOOL WITH MULTIPLE PUNCTURE NEEDLES

(75) Inventors: Hisataka Harada, Fukuroi (JP);
Hidetomo Mikami, Fukuroi (JP);
Mihoko Suzuki, Fukuroi (JP)

(73) Assignee: Covidien LP, Mansfield, MA (US)

( * ) Notice: Subject to any disclaimer, the term of this patent is extended or adjusted under 35 U.S.C. 154(b) by 1208 days.

(21) Appl. No.: 11/867,742

(22) Filed: Oct. 5, 2007

(65) Prior Publication Data

US 2008/0255591 A1    Oct. 16, 2008

(30) Foreign Application Priority Data

Oct. 5, 2006    (JP) .................................. 2006-273779

(51) Int. Cl.
| | |
|---|---|
| A61B 17/12 | (2006.01) |
| A61B 17/04 | (2006.01) |
| A61B 17/06 | (2006.01) |
| A61B 19/00 | (2006.01) |

(52) U.S. Cl.
CPC ..... *A61B 17/0469* (2013.01); *A61B 2017/0446* (2013.01); *A61B 2017/06042* (2013.01); *A61B 2017/045* (2013.01); *A61B 2017/0464* (2013.01); *A61B 17/0482* (2013.01); *A61B 2017/06052* (2013.01); *A61B 2017/0404* (2013.01); *A61B 2017/0496* (2013.01); *A61B 17/0487* (2013.01); *A61B 19/44* (2013.01); *A61B 17/0485* (2013.01); *A61B 2017/0472* (2013.01)
USPC .......................................... 606/144; 606/148

(58) Field of Classification Search
USPC .................. 606/139, 144, 148, 157, 232, 215
See application file for complete search history.

(56) References Cited

U.S. PATENT DOCUMENTS

| | | | |
|---|---|---|---|
| 2,012,776 | A | 8/1935 | Roeder |
| 4,935,027 | A | 6/1990 | Yoon |
| 5,037,433 | A | 8/1991 | Wilk |
| 5,052,396 | A | 10/1991 | Wedel et al. |
| 5,100,387 | A | 3/1992 | Ng |
| 5,123,914 | A | 6/1992 | Cope |
| 5,242,427 | A | 9/1993 | Bilweis |
| 5,251,873 | A | 10/1993 | Atkinson et al. |
| 5,281,237 | A | 1/1994 | Gimpelson |
| 5,330,488 | A | 7/1994 | Goldrath |
| 5,336,229 | A | 8/1994 | Noda |

(Continued)

FOREIGN PATENT DOCUMENTS

| | | |
|---|---|---|
| DE | 2900265 A1 | 7/1980 |
| EP | 0246836 A2 | 11/1987 |

(Continued)

OTHER PUBLICATIONS

Extended European Search Report, Application No. 07117964.2-2310, dated Feb. 22, 2008, 10 pages.

*Primary Examiner* — Tuan V Nguyen
(74) *Attorney, Agent, or Firm* — Lisa E. Winsor, Esq.

(57) ABSTRACT

A suture tool for fixing the gastric wall to the abdominal wall includes a first puncture needle for insertion, a suture thread, a second puncture needle for removing the suture thread, a linear grasping member and one or more anchor member. The tip end portion of the suture thread is inserted into the first puncture needle and a hook of the linear grasping member is inserted into the second puncture needle for removing the suture thread inserted into the first puncture needle for securing the gastric wall to the abdominal wall.

11 Claims, 15 Drawing Sheets

(56) References Cited

U.S. PATENT DOCUMENTS

| | | |
|---|---|---|
| 5,336,231 A | 8/1994 | Adair |
| 5,364,410 A | 11/1994 | Failla et al. |
| 5,389,082 A | 2/1995 | Baugues et al. |
| 5,391,182 A | 2/1995 | Chin |
| 5,462,560 A | 10/1995 | Stevens |
| 5,499,991 A | 3/1996 | Garman et al. |
| 5,501,691 A | 3/1996 | Goldrath |
| 5,531,699 A | 7/1996 | Tomba et al. |
| 5,569,269 A * | 10/1996 | Hart et al. .................. 606/144 |
| 5,626,590 A * | 5/1997 | Wilk ............................ 606/148 |
| 5,653,716 A * | 8/1997 | Malo et al. ................... 606/139 |
| 5,665,096 A | 9/1997 | Yoon |
| 5,681,333 A | 10/1997 | Burkhart et al. |
| 5,722,981 A | 3/1998 | Stevens |
| 5,728,109 A | 3/1998 | Schulze et al. |
| 5,741,276 A | 4/1998 | Poloyko et al. |
| 5,782,845 A | 7/1998 | Shewchuk |
| 5,817,111 A * | 10/1998 | Riza ............................. 606/148 |
| 5,895,395 A | 4/1999 | Yeung |
| 5,897,563 A | 4/1999 | Yoon et al. |
| 5,921,993 A | 7/1999 | Yoon |
| 5,938,668 A | 8/1999 | Scirica et al. |
| 5,993,434 A | 11/1999 | Dev et al. |
| 6,022,360 A | 2/2000 | Reimels et al. |
| 6,036,700 A | 3/2000 | Stefanchik et al. |
| 6,066,146 A | 5/2000 | Carroll et al. |
| 6,110,183 A | 8/2000 | Cope |
| 6,113,068 A | 9/2000 | Ryan |
| 6,113,610 A | 9/2000 | Poncet |
| 6,113,611 A | 9/2000 | Allen et al. |
| RE36,974 E | 11/2000 | Bonutti |
| 6,156,056 A | 12/2000 | Kearns et al. |
| 6,500,184 B1 * | 12/2002 | Chan et al. .................. 606/144 |
| 6,524,317 B1 | 2/2003 | Ritchart et al. |
| 6,638,286 B1 | 10/2003 | Burbank et al. |
| 7,306,613 B2 | 12/2007 | Kawashima et al. |
| 7,320,693 B2 | 1/2008 | Pollack et al. |
| 7,731,726 B2 * | 6/2010 | Belhe et al. ................. 606/148 |
| 7,918,868 B2 | 4/2011 | Marshall et al. |
| 2002/0147456 A1 | 10/2002 | Diduch et al. |
| 2003/0004523 A1 | 1/2003 | Chan et al. |
| 2003/0109883 A1 | 6/2003 | Matsuzaki et al. |
| 2003/0191497 A1 | 10/2003 | Cope |
| 2004/0039442 A1 | 2/2004 | St. Goar et al. |
| 2004/0098050 A1 | 5/2004 | Foerster et al. |
| 2004/0122473 A1 | 6/2004 | Ewers et al. |
| 2004/0249393 A1 | 12/2004 | Weisel et al. |
| 2004/0249395 A1 | 12/2004 | Mikkaichi et al. |
| 2005/0288689 A1 | 12/2005 | Kammerer et al. |
| 2006/0069398 A1 | 3/2006 | Suzuki et al. |
| 2007/0023305 A1 | 2/2007 | Chan et al. |
| 2007/0118153 A1 | 5/2007 | Funamura et al. |
| 2007/0179509 A1 | 8/2007 | Nagata et al. |
| 2007/0282351 A1 | 12/2007 | Harada et al. |
| 2007/0293876 A1 | 12/2007 | Abe et al. |
| 2008/0228204 A1 | 9/2008 | Hamilton et al. |
| 2008/0243147 A1 | 10/2008 | Hamilton et al. |

FOREIGN PATENT DOCUMENTS

| | | |
|---|---|---|
| EP | 0706779 A1 | 4/1996 |
| EP | 0717957 A1 | 6/1996 |
| EP | 1598017 A1 | 11/2005 |
| EP | 1844718 A1 | 10/2007 |
| JP | 61205510 U | 12/1986 |
| JP | 04226643 | 8/1992 |
| JP | 05-161655 A | 6/1993 |
| JP | 06-024533 B2 | 4/1994 |
| JP | 06044511 U | 6/1994 |
| JP | 07-328020 | 12/1995 |
| JP | 2002336262 A | 11/2002 |
| JP | 3331215 B1 | 8/2003 |
| JP | 2004141646 A | 5/2004 |
| JP | 2005270332 A | 10/2005 |
| JP | 2006025932 | 2/2006 |
| JP | 2006025933 | 2/2006 |
| JP | 2006025934 | 2/2006 |
| JP | 2006151429 | 5/2006 |
| WO | 9421178 A1 | 9/1994 |
| WO | 95/22932 A1 | 8/1995 |
| WO | 0145570 A1 | 6/2001 |
| WO | 2004006782 A1 | 4/2004 |
| WO | 2005094697 A1 | 10/2005 |
| WO | 2006037639 A1 | 4/2006 |
| WO | 2006082810 A1 | 10/2006 |
| WO | 2007018520 A1 | 2/2007 |

* cited by examiner (a)

(b)

MEDICAL SUTURING TOOL WITH MULTIPLE PUNCTURE NEEDLES

FIELD OF THE INVENTION

The invention relates to a suture tool of medical use for suturing a suture site of an organ and a skin side portion in a patient to be sutured.

BACKGROUND OF THE INVENTION

In conventional, a suture tool of medical use has been used to suture and secure a suture site, in particular, a suture site comprising an organ and a skin side portion. For example, though a gastrostomy tube has been applied to a person whose food intake function by himself at mouth is decreased due to his advanced age or disease to supply fluid drink or food such as fluid diet or nutritional supplement into the stomach, this gastrostomy tube is attached by forming a hole at the stomach of the patient. In this case, to properly perform the attachment of the gastrostomy tube, the abdominal wall and the gastric wall are immobilized by using the suture tool of medical use (For example, see Patent Literature 1).

This suture tool of medical use comprises two puncture needles positioned in parallel with an interval maintained. When a suture is performed, firstly these two puncture needles are a penetrated into the suture site to be sutured of the patient at the same time. Next, a suture is passed through one of the needles and an intra needle to which a loop body comprised of a wire is connected at the tip end portion is passed through the other needle, the intra needle is pulled out of the patient while the suture is grasped by the loop body in the patient's body. Then, after pulling two puncture needles out of the patient, both end portions of the suture being outside of the patient's body are tied up to complete the suture. Also, the tip end of the puncture needle into which the intra needle is inserted is formed to be curved such that the tip end opening is oriented toward a side, whereby the loop body is projected to the outside while being horizontally extended as the intra needle is inserted into the puncture needle, thereby grasping the suture. See for example Japanese Patent Unexamined Publication No. H5-161655

However, in the conventional suture tool of medical use, there are problems of that the puncture needle is difficult to be penetrated due to its curved tip end, or that the operation to tie up the suture external body of the patient is complicated. Further, there is another problem of that the operation for the engagement of the loop body with the suture is complicated because the suture must be passed through the small loop body.

The invention has been made in the light of these problems and the object of the invention is to provide a suture tool of medical use which is easy to handle and provide the improved safety of the suture.

SUMMARY OF THE INVENTION

In one aspect of the present invention, the configurational characteristics of the suture tool is that the suture tool of medical use for fixing an organ to a skin side portion comprises a first puncture needle for insertion being capable of penetrating from the skin side portion into the organ and having an insertion hole formed therein; a suture inserted from the basal end opening into said puncture needle for insertion and being capable of being protruded from the tip end opening of said puncture needle. This allows for insertion at the tip end side of the suture; a second puncture needle for taking out being capable of penetrating from the skin side portion into the organ with keeping the predetermined space apart from the puncture needle for insertion and having an insertion hole formed therein; a linear grasping member capable of being inserted from the basal end opening of the insertion hole of the puncture needle for taking out and engaged with the tip end portion of the suture by protruding the tip end portion of the member; and a anchor member for preventing the suture from dragging into the skin side portion by engaging respective suture as pulled of the puncture needle for insertion, the puncture needle for taking out and the linear grasping member out of the organ and the skin side portion.

Various refinements exist of the features noted in relation to the above-mentioned aspects of the present invention. Further features may also be incorporated in the above-mentioned aspects of the present invention as well. These refinements and additional features may exist individually or in any combination. For instance, various features discussed below in relation to any of the illustrated embodiments of the present invention may be incorporated into any of the above-described aspects of the present invention, alone or in any combination.

DESCRIPTION OF REFERENCE NUMBERS 11 represents the puncture needle for insertion outer tube; 11a, 12a and 21a represent the insertion holes; 11b and 21b represent the openings; 12 represents the puncture needle for insertion inner tube; 13 represents the suture thread; 13a represents the basal end portion; 13b represents the tip end portion; 21 represent the puncture needle for taking out; 22 represents the linear grasping member; 26 represents the hook; 26a represents the engagement portion; 30, 30a 30b 40 and 40a represent anchor members; 31a, 31b, 35a and 35b represent slits; 32a, 32b 36a and 36b represents stopping holes; 33 represents the abdominal wall; 34 represents the gastric wall; and A represents the suture tool of medical use.

DETAILED DESCRIPTION OF THE INVENTION

Figure 1:
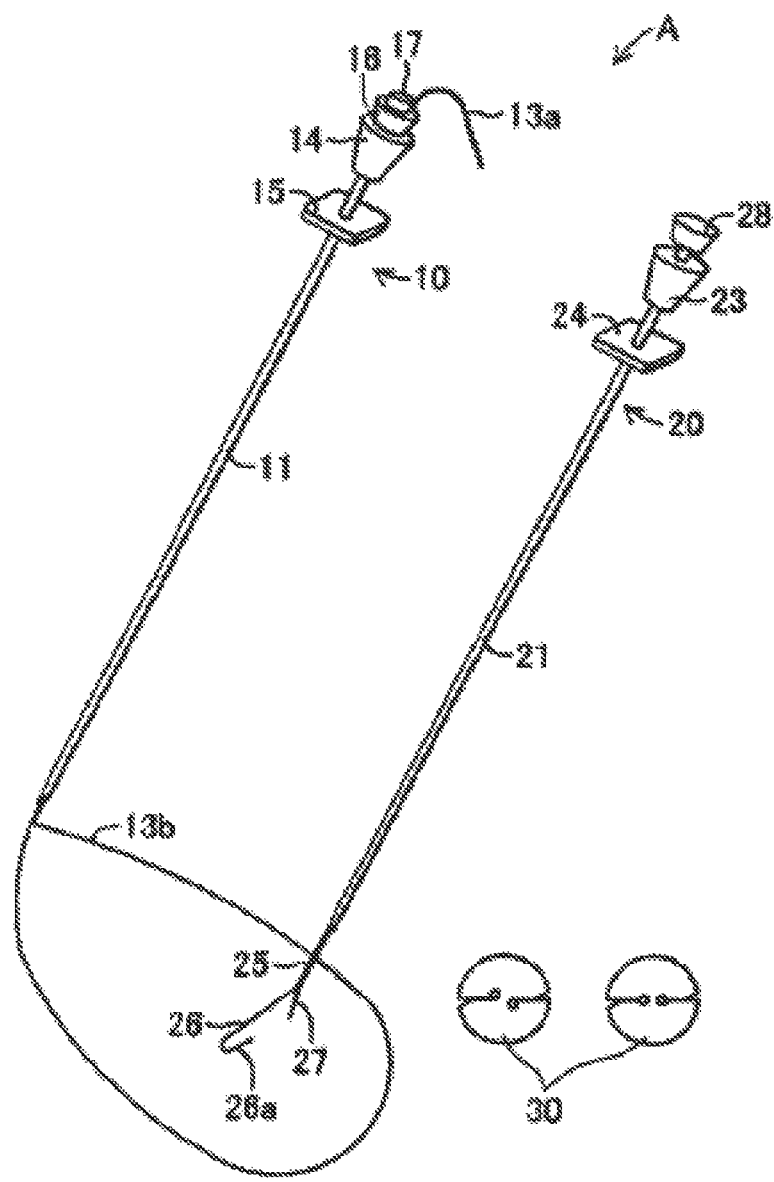
FIG. 1 is a perspective view illustrating the suture tool of medical use of one embodiment of in accordance with the invention.
Figure 2:
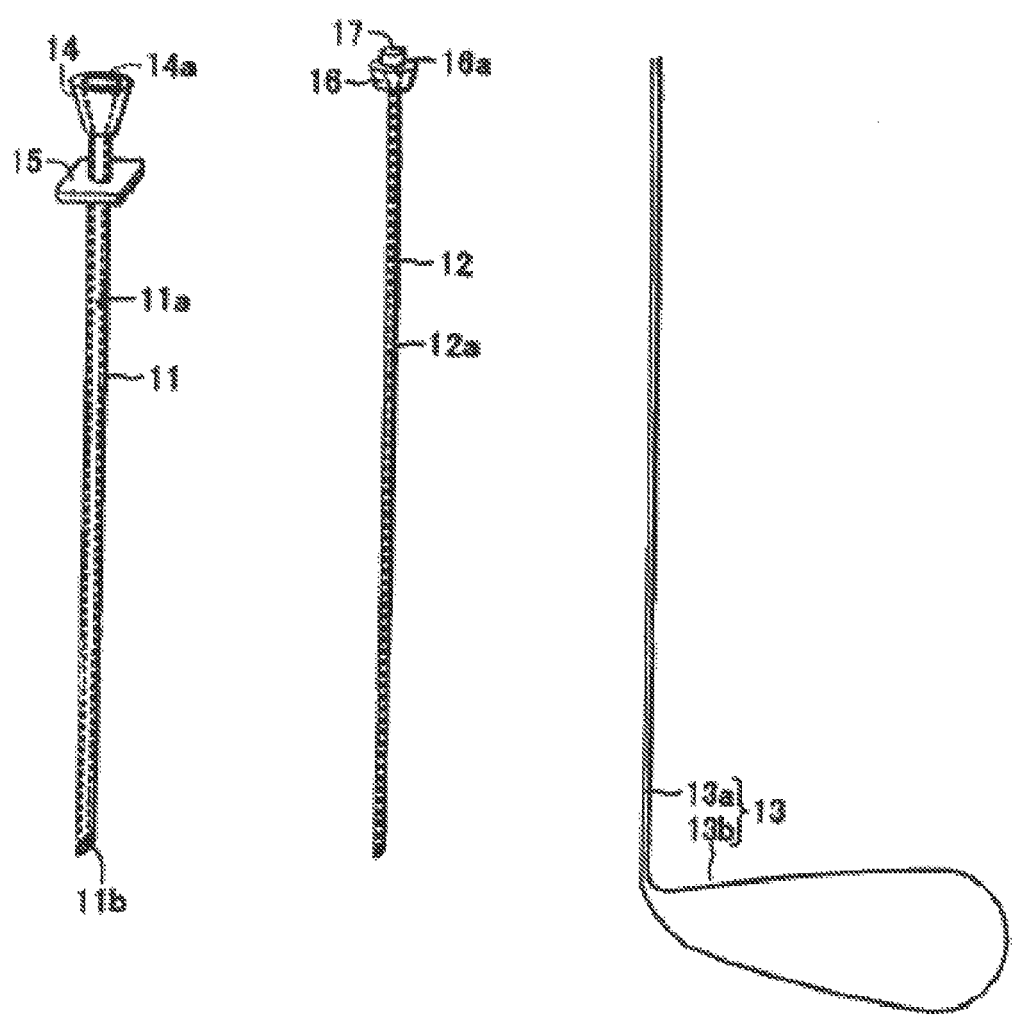
FIG. 2 is an exploded perspective view illustrating the thread inserting member.

The suture tool of medical use of one embodiment in accordance with the invention will now be explained in detail with the reference to the drawings in below. FIG. 1 shows a suture tool of medical use A of the embodiment in accordance with the invention. The suture tool of medical use A comprises a suture thread inserting member 10, a suture thread taking out member 20 and two anchor members 30. And the suture thread inserting member 10 includes, as shown in FIG. 2, a puncture needle for insertion outer tube 11, a puncture needle for insertion inner tube 12 and a suture thread 13. The puncture needle for insertion outer tube 11 is formed by a cylindrical body made of stainless steel provided with an insertion hole 11a through which the puncture needle for insertion inner tube 11 is inserted into the inside thereof and a hub 14 made of resin at the basal end (upper end) thereof.

The hub 14 is formed into a cylinder in which the diameter of the upper portion is greater than that of the lower portion and provided with a guide hole 14a communicating with the insertion hole 11a at the inside thereof. The guide hole 14a is formed such that the diameter of the upper portion is greater than that of the lower portion thereof along the outer peripheral surface of the hub 14, whereby the puncture needle for insertion inner tube 12 can readily be inserted from the upper of the hub 14 into the insertion hole 11a of the puncture needle for insertion outer tube 11. Moreover, the tip end (lower end) of the puncture needle for insertion outer tube 11 is beveled off, whereby opening 11b is formed such that it can be seen from the lateral direction.

Further, to the lower of the hub 14 in the puncture needle for insertion outer tube 11, a holding part 15 having a rectangular shape spaced apart from the hub 14 is mounted. The holding part 15 is used as a grasping part together with the hub 14 at the operation of the puncture needle for insertion outer tube 11 and installed to the puncture needle for insertion outer tube 11 by inserting the puncture needle for insertion outer tube 11 into a hole formed at the center thereof. Also, the install position of the holding part 15 to the puncture needle for insertion outer tube 11 is properly set according to the quantity of the protrusion (the length for inserting into the suture site) of the portion of the puncture needle for insertion outer tube 11 lower than the holding part 15.

The puncture needle for insertion inner tube 12 is capable of being inserted into the insertion hole 11a of the puncture needle for insertion outer tube 11 and formed by a cylindrical body having a small diameter made of stainless steel to which an insertion hole 12a through which the suture thread 13 is inserted in the inside is provided and a hub 16 made of a resin is mounted to the basal end (upper end) thereof. The hub 16 is formed into a cylinder in which the diameter of the upper side is greater than that of the lower side and provided with a guide hole 16a communicating with the insertion hole 12a at the inside thereof.

This guide hole 16a is formed such that the diameter of the upper side is greater than that of the lower side along with the outer peripheral surface of the hub 16, whereby the suture thread 13 can easily be inserted from the upper of the hub 16 into the insertion hole 12a of the puncture needle for insertion inner tube 12. Further, to the upper side portion of the guide hole 16a in the hub 16, a plug like thread stopper 17 for fixing the suture thread 13 to be inserted from the guide hole 16a into the insertion hole 12a is detachably provided. The puncture needle for insertion of the invention is comprised by this puncture needle for insertion inner tube 12 and the puncture needle for insertion outer tube 11.

The suture thread 13 is comprised by a fine line made of a resin material which is formed such that one fine line is folded into a double-line to provide a ring by the folded portion at the center. Also, straight portions at both ends of the fine line configure a basal end portion 13a and the ring portion at the center configures a tip end portion 13b, as well as, the tip end portion 13a is formed so as to generally perpendicular relative to the basal end portion 13a. This suture thread 13 is of flexibility and easily deformed by applying a light force and is restored to the original shape (shape illustrated in FIG. 2) as the force deforming it is released.

Figure 3:
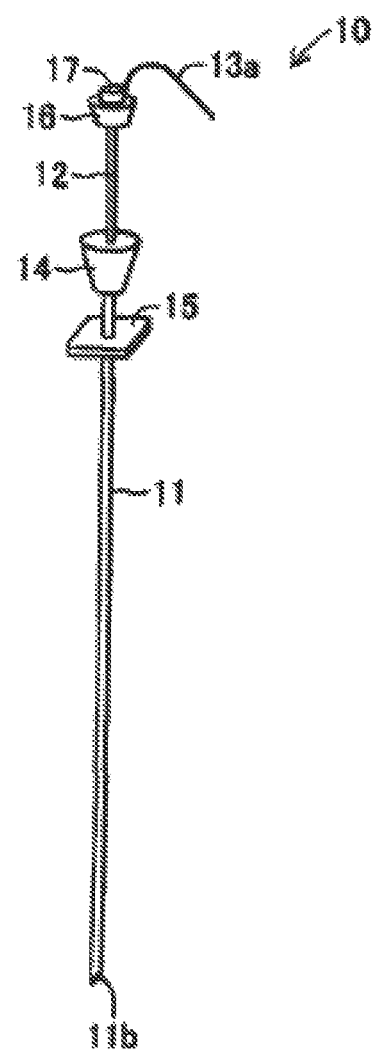
FIG. 3 is a perspective view illustrating the condition of the thread inserting member installed.

Therefore, when the tip end portion 13b of the suture thread 13 is stretched into a linear line and inserted from the guide hole 16a of the hub 16 into the insertion hole 12a of the puncture needle for insertion inner tube 12, the tip end portion 13b of the suture thread 13 travels toward the lower end opening within the insertion hole 12a while it makes a linear line with the basal end portion 13a. And, the suture thread 13 is fixed by the thread stopper 17 as the tip end of the tip end portion 13b is closed to the lower end opening of the puncture needle for insertion inner tube 12 and the puncture needle for insertion inner tube 12 in this condition is inserted from the guide hole 14a of the hub 14 into the insertion hole 11a of the puncture needle for insertion outer tube 11, thereby providing the condition as shown in FIG. 3. According to this, the thread inserting member 10 can be penetrated into a body of a patient.

Figure 4:
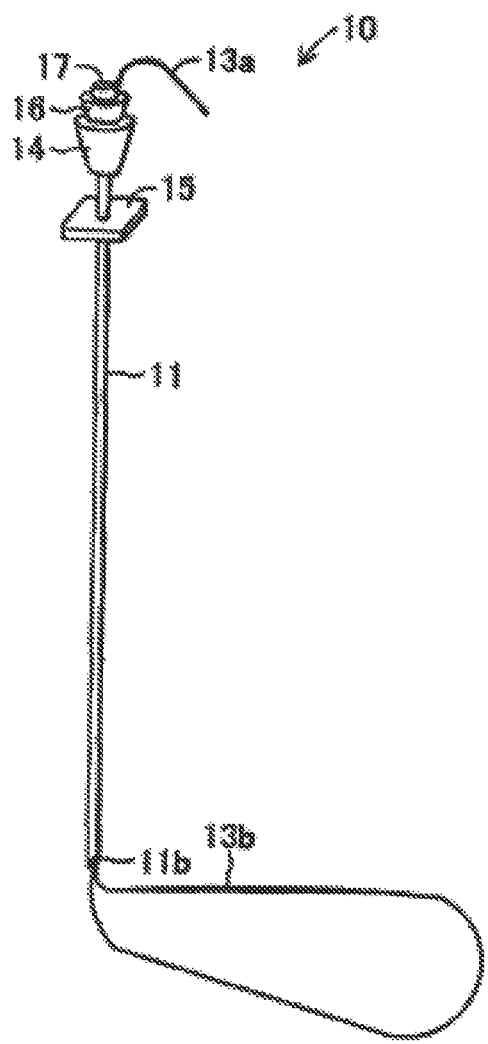
FIG. 4 is a perspective view illustrating the condition in which the suture thread is protruded from the opening of the puncture needle for insertion outer tube in the thread inserting member.

Further, from this condition, when the basal end portion 13a of the suture thread 13 is inserted into the puncture needle for insertion inner tube 12 by loosing the thread stopper 17, the tip end portion 13b of the suture thread 13 is projecting from the opening 11b of the puncture needle for insertion outer tube 11. Then, when the whole of the tip end portion 13b is projected to the outside of the puncture needle for insertion outer tube 11 from the opening 11b, the tip end portion 13b is extended in the lateral direction generally perpendicular to the puncture needle for insertion outer tube 11 to be the ring. In this condition, the thread inserting member 10 is maintained in the condition as shown in FIG. 4 by tightening the suture thread 13 by pressing the thread stopper 17 to the hub 16.

Figure 5:
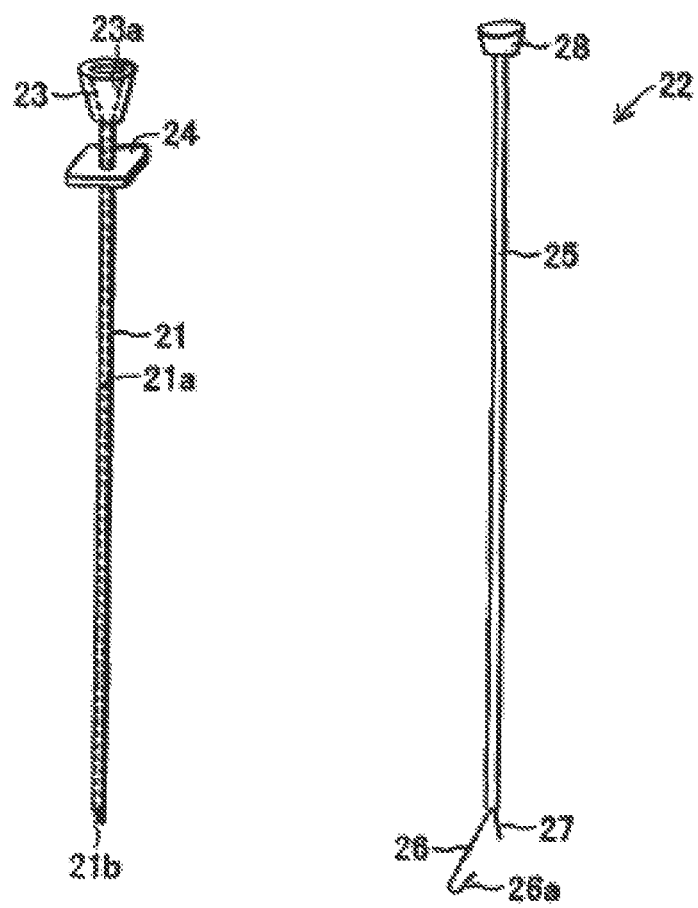
FIG. 5 is an exploded perspective view illustrating the thread inserting member.

The thread taking out member 20, as shown in FIG. 5, comprises a puncture needle for taking out 21 and a linear grasping member 22. The puncture needle for taking out 21 is comprised by a cylindrical body made of stainless steel to which an insertion hole 21a through which the linear holding member 22 is inserted is formed at the inside thereof and a hub 23 made of a resin is provided at the basal end (upper end) portion thereof. This hub 23 is formed into a cylinder in which the diameter of the upper side is greater than that of the lower side and provided with a guide hole 23 communicating with the insertion hole 21a at the inside thereof. This guide hole 23a is formed such that the diameter of the upper side is greater than that of the lower side along with the outer peripheral surface of the hub 23, whereby the linear grasping member 22 can readily be inserted from the upper of the hub 23 into the insertion hole 21a of the puncture needle for taking out 21. Further the tip end (lower end) of the puncture needle for taking out is beveled and an opening 21b formed by this beveled portion is formed so as to be seen from the lateral direction.

Moreover, to the lower of the hub 23 of the puncture needle for taking out 21, a rectangular plate like holding part 24 is attached. This holding part 24 together with the hub 23 is used as a grasping part at the operation of the puncture needle for taking out 21 and attached to the puncture needle for taking out 21 by inserting the puncture needle for taking out 21 into a hole formed at the center part. The attachment position of the holding part to the puncture needle for taking out 21 is properly set according to the quantity of the puncture needle for taking out 21 lower than the holding part 24.

The linear holding part 22 comprises an intra needle 25 made of stainless steel having a small diameter being capable of inserting within the insertion hole 21a of the puncture needle for taking out 21, a hook 26 obliquely downwardly extended from the tip end of the intra needle 25, a guide part 27 obliquely downwardly extended from the tip end of the intra needle 25 in the opposite direction where the hook 26 is extended, and a grasping part 28 attached to the basal end of the intra needle 25. The hook 26 is comprised by a very fine line body more fine than the intra needle 25 and the tip end thereof is bended and comprised by an engagement part 26a capable of being engaged with the suture thread 13.

Figure 6:
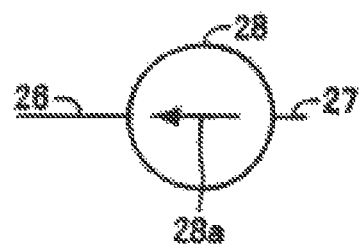
FIG. 6 is a plan view illustrating the linear grasping member.

Further, the guide portion 27 is comprised by a straight line body having the same diameter as that of the hook 26 and a shorter length than that of the hook 26 which is provided for the easy visibility the direction where the hook 26 I extended. The hook 26 and the guide part 27 are of flexibility whereby they are easily deformed to extend and straighten by applying a light force thereto such that they are closed each other and they are restored to their original shapes (shapes illustrated in FIG. 5) as widened the distance between them by releasing the deforming force. The grasping part 28 is comprised by a generally cylindrical resin material. In the upside view of the grasping part 28, as shown in FIG. 6, an allow 28a indicating the direction of the hook 26 extending.

Figure 7:
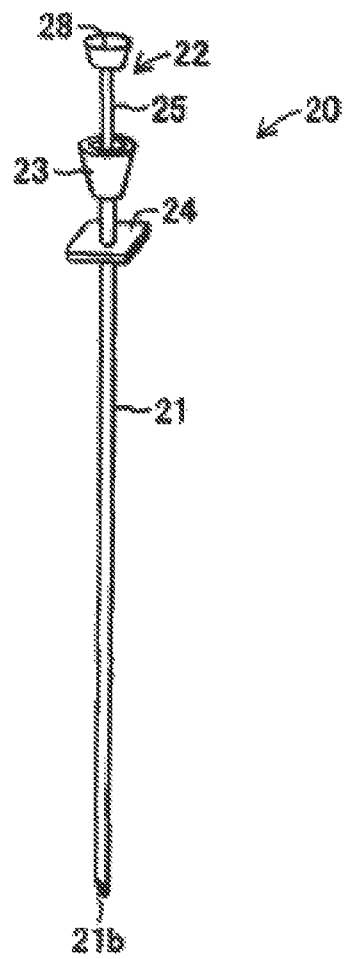
FIG. 7 is a perspective view illustrating the condition in which the thread taking out member is installed.

Accordingly, when the hook 26 and the guide 27 are stretched into a straight line by pressing so as to close each other and inserted from the guide hole 23a of the hub 23 into the insertion hole 21a of the puncture needle for taking out 21 as well as the intra needle 25 is inserted into the insertion hole 21a, the hook 26 and the guide part 27 together travel toward the opening 21a within the insertion hole 21a with the straight line form maintained. Then, as the engagement part 26a of the hook 26 is closed to the opening 21b of the puncture needle for taking out 21, the condition as shown in FIG. 7 can be provided by stopping the insertion of the linear grasping member 22 into the puncture needle for taking out 21. Therefore, the thread taking out member 20 can be penetrated into the body of the patient.

Figure 8:
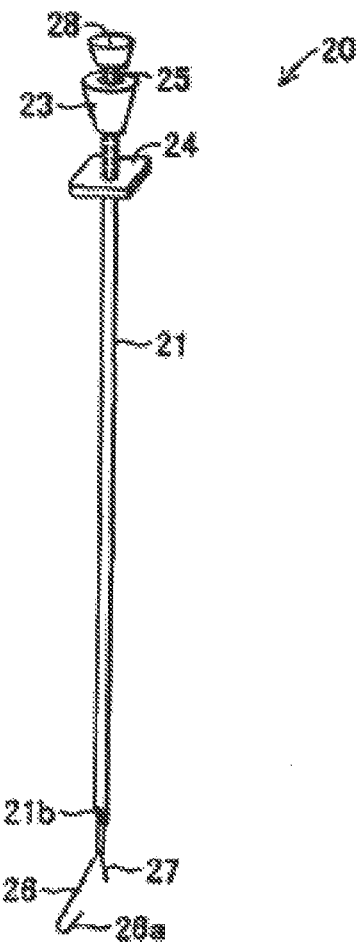
FIG. 8 is a perspective view illustrating the condition in which the hook and the guide part is protruded from the opening of the puncture needle for taking out in the thread taking out member.

Further, from this condition, when the linear grasping member 22 is further inserted into the inside of the puncture needle for taking out, the hook 26 and the guide part 27 are projecting from the opening 21b of the puncture needle for taking out 21. Then, when the whole the hook 26 and the guide part 27 are projected to the outside of the puncture needle for taking out 21 at the opening 21b, the hook 26 and the guide part 27 are downwardly extended in the opposite directions, respectively, to be in the condition as shown in FIG. 8. When the hook 26 and the guide part 27 are viewed from the upside, they are in a straight line as shown in FIG. 6. At that time directions of the hook 26 and the allow 28a are matched.

Figure 9:
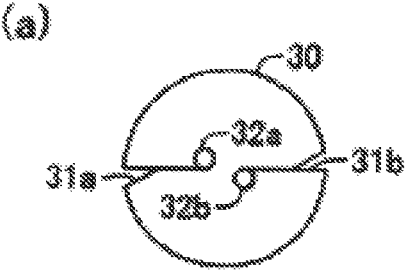
FIG. 9 shows the anchor members; (a) is a plan view and (b) is a side view thereof.
Figure 9:
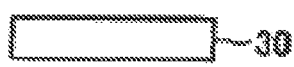
Figure 10:
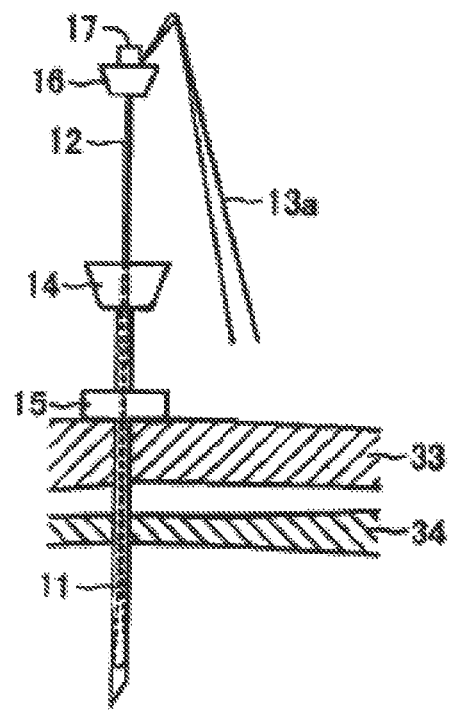
FIG. 10 is a cross sectional view illustrating the thread inserting member penetrated into the stomach portion.

The anchor member 30, as shown in FIG. 9, is comprised by a resin material formed into a generally disk like shape and slits 31a and 31b extended from the outer peripheral toward the center are formed at both sides sandwiching the central potion of the disk like shape. Small stopping holes 32a and 32b for stopping the suture thread 13 are formed at the deeper end of these slits 31a and 31b, respectively. The slit 31a is notched at the lower end in the condition as shown in FIG. 9(a) in the outer periphery portion to form a V shape in which the width thereof is decreased from the outer periphery side to the deeper end side and the deeper end portion is comprised by a notch formed into a line.

Also, the stopping hole 32a is formed in series with the slit 31a at the upper of the deeper end of the slit 31a. Further, the slit 31b is notched at the upper side in the outer periphery portion in the condition as shown in FIG. 9(a), to form a V shape in which the width thereof is decreased from the outer periphery side to the deeper end side and the deeper end portion is comprised by a notch formed into a line. The stopping hole 32b is formed in series with the slit 31b at the upper of the deeper end of the slit 31b. Accordingly, when the suture thread 13 is engaged with the anchor member 30, the suture thread 13 is passed from the V shaped portions of wider at the outer sides through line portions of slits 31a and 31b to engage with stopping holes 32a and 32b.

Moreover, since stopping holes 32a and 32b are formed at deviated position from the line in which slits 31a and 31b are extended in a straight line, the suture thread 13 engaged with stopping holes 32a and 32b is difficult to be released from the anchor member 30. Also, the notch parts of the invention are comprised by the slit 31a and the stopping hole 32a and the slit 31b and the stopping hole 32b, respectively. The suture tool of medical use A configured in this way may be used in combination with other one or more sets of thread taking out member 20, in hit case, the number of the anchor members 30 are increased as adjusted to the increased number of the thread taking out member 20.

Next, to the suture tool of medical use A, one set of the thread taking out member 20 and one anchor member 30 are added and the suture tool of medical use comprising one set of thread inserting member 10, two sets of thread taking out member 20 and three anchor members 30 is used to explain a case where, for example, an abdominal wall 33 as the skin side portion of the invention and a gastric wall 34 as a wall of the organ of the invention in the patient (see FIGS. 10 to 18) are sutured. In this suture, firstly, the thread inserting member 10 in the condition as shown in FIG. 3 is pressed into the skin surface in the stomach of the patient to penetrate the tread inserting member 10 into the abdominal wall 33 and the gastric wall 34.

Figure 11:
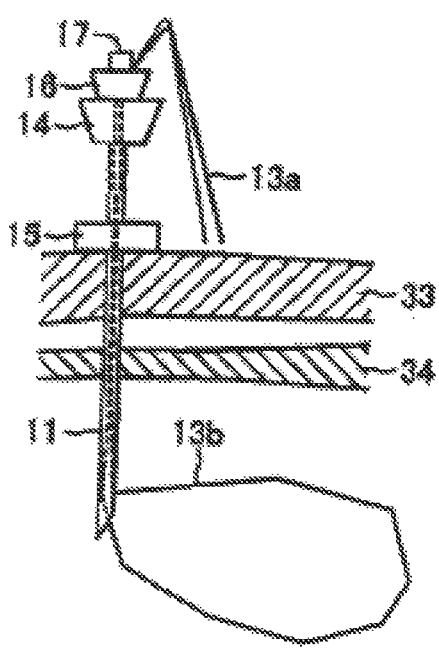
FIG. 11 is a cross sectional view illustrating the tip end portion of the suture thread extended within the stomach.

In FIGS. 10 to 17, each component of the suture tool of medical use is simplified and, therefore, the size or shape of each component thereof is different from each component of the suture tool of medical use A shown in FIG. 1 and the like. In this case, the tread inserting member 10 is penetrated until the holding part 15 is contacted to the skin surface of the abdominal wall 33 whereby the opening 11b of the puncture needle for insertion outer tube 11 is positioned within the gastric wall 34. Then, the basal end portion 13a of the suture thread 13 is inserted into the puncture needle for insertion inner tube 12 by loosing the thread stopper 17 so that the tip end portion 13b of the suture thread 13 is projected to the opening 11b of the puncture needle for insertion outer tube 11. As a result, the tip end portion 13b is extended so as to be generally perpendicular to the puncture needle for insertion outer tube 11 within the gastric wall 34 to be the ring as shown in FIG. 11. In this condition, the thread stopper 17 is pressed to the hub 16 to tighten and fix the suture thread 13.

Figure 12:
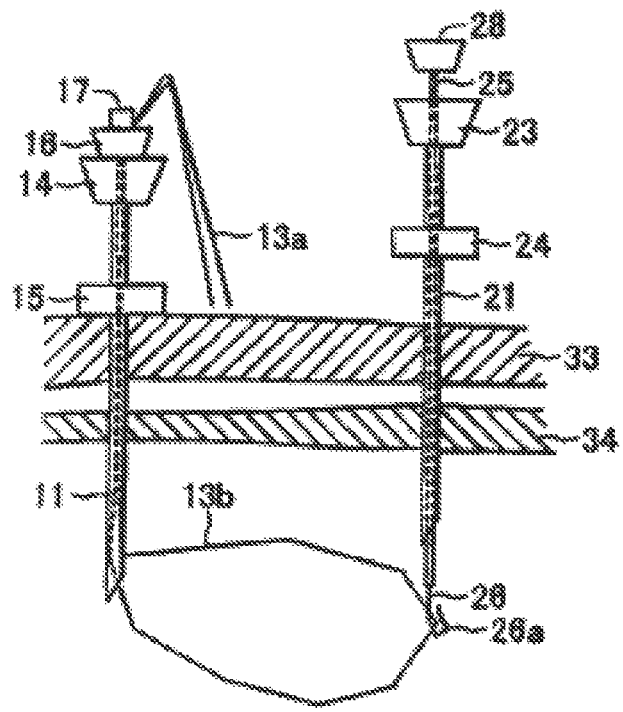
FIG. 12 is a cross sectional view illustrating the condition in which the hook of the linear grasping member is engaged with the tip end portion of the suture thread.

Then, the tread taking out member 20 as shown in FIG. 7 is pressed to the skin surface in the stomach of the patient while the predetermined distance from the thread inserting member 10 is maintained and penetrated into the abdominal wall 33 and the gastric wall 34. Next, the grasping part 28 of the linear holding member 22 is pressed to the inside of the puncture needle for taking out 21 to project the hook 26 and the guide part 27 from the opening 21b of the puncture needle for taking out 21. Accordingly, the hook 26 and the guide part 27 downwardly travel to near the tip end portion 13b of the suture thread 13 while being extended within the gastric wall 34 and the hook 26 and the guide part 27 sandwich the predetermined portion of the tip end portion 13b, thereby providing the condition as shown in FIG. 12.

In this case, the operation is conducted by observing the tip end portion 13b of the suture thread 13, hook 26 and the guide part 27 with an endoscope to engage the tip end portion 13b of the suture thread 13 with the engagement part 26a of the hook 26. At that time, the operation is also performed while determining the position of the hook 26 with the allow 28a indicated on the upside view of the grasping part 28 in the linear grasping member 22. Then, the grasping part 28 is upwardly pulled up to move the linear grasping member 22 to the basal end side of the puncture needle for taking out 21. At that time, the hook 26 engaged with the tip end portion 13b of the suture thread 13, together with the guide part 26, enters the puncture needle for taking out 21 to press the tip end portion 13b of the suture thread 13 against the edge portion of the opening 21b.

Figure 13:
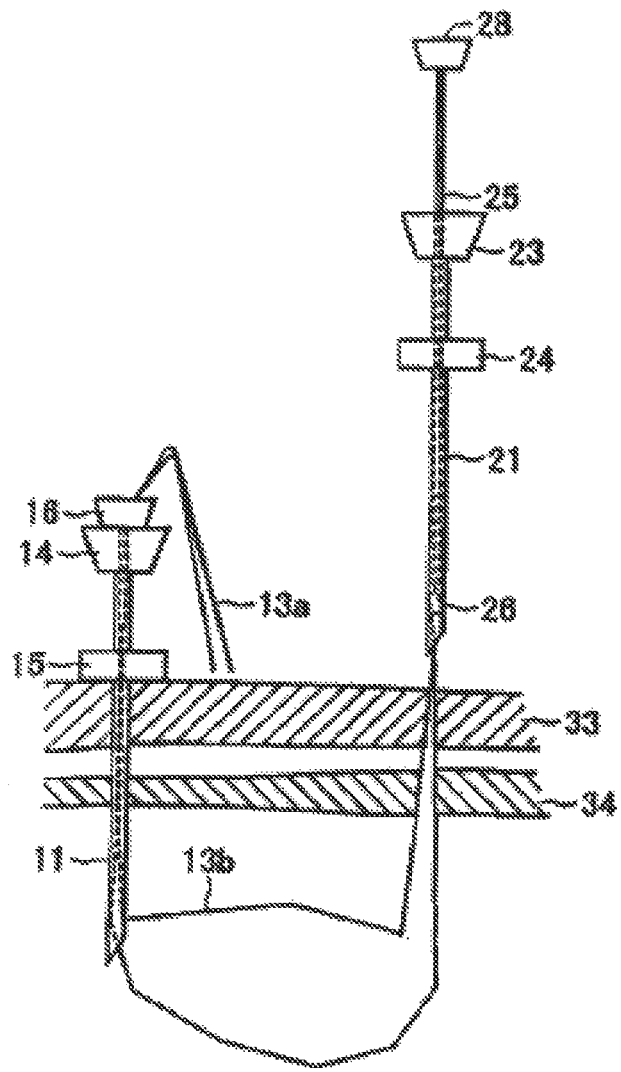
FIG. 13 is a cross sectional view illustrating the thread taking out member pulled out of the stomach.
Figure 14:
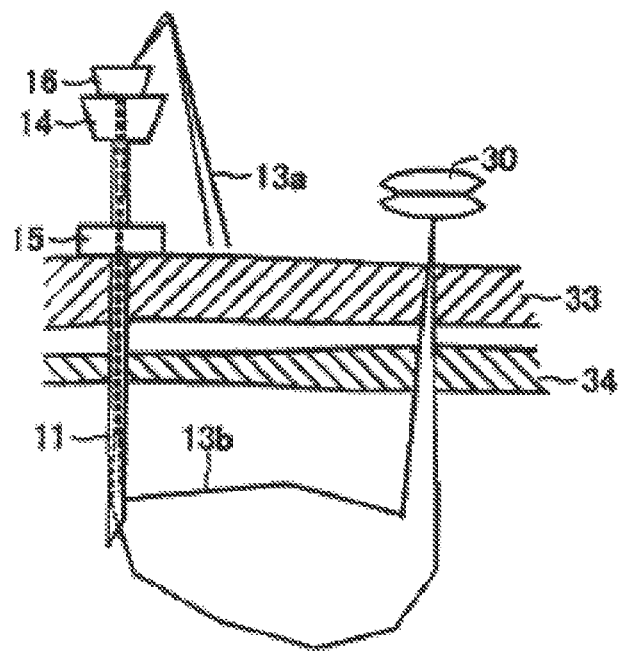
FIG. 14 is a cross sectional view illustrating the suture thread anchored by the anchor member.

According to this, the tip end portion 13b of the suture thread 13 is engaged with the edge portion of the opening 21b and, then, in this condition, the thread taking out member 20 is pulled out of the body of the patient, whereby one part of the tip end portion 13b of the suture thread 13 is passed through the gastric wall 34 and the abdominal wall 33 to protrude from the body of the patient as shown in FIG. 13. Then, the hook 26 is released from the tip end portion 13b of the suture thread 13 and the anchor member 30 is mounted thereto to provide the condition of FIG. 14. In this case, the anchor member 30 is disposed within the ring of the one portion of the tip end portion 13b that has been protruded from the body of the patient such that the anchor member 30 is surrounded by the tip end portion 13b, then, portions of the tip end portion 13b opposed to slits 31a and 31b, respectively, are conducted into slits 31a and 31b to engage those portions with the sopping hole 32a and 32b, thereby mounting the anchor member 30 to the tip end portion 13b of the suture thread 13.

Figure 15:
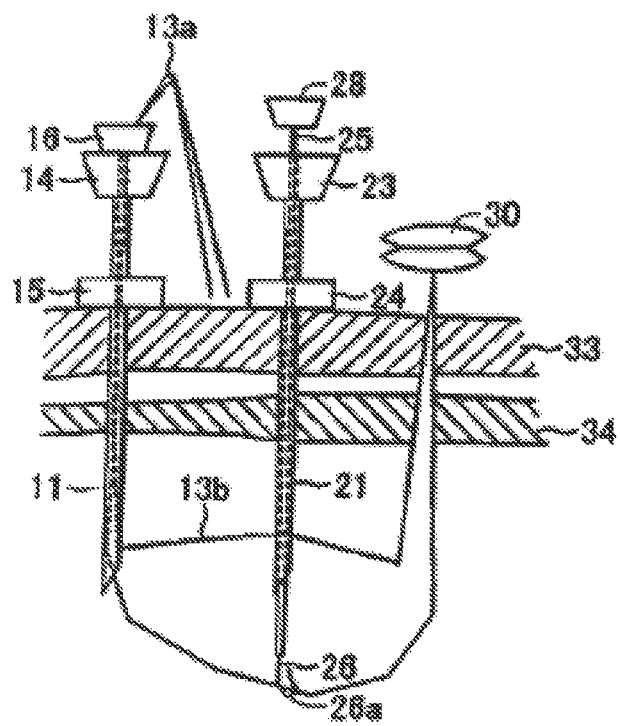
FIG. 15 is a cross sectional view illustrating another thread inserting member penetrated into the stomach.

Next, the other one set of thread taking out members 20 is positioned in the condition as shown in FIG. 7 and pressed into the skin surface in the stomach of the patient while each member 20 keeps the predetermined distance from the thread inserting member 10 and the anchor member 30 mounted to the stomach of the patient, respectively, and penetrated into the abdominal wall 33 and the gastric wall 34. Then, the grasping part 28 of the linear grasping member 22 included in the thread taking out members 20 is pressed against the inside of the puncture needle for taking out 21 to protrude the hook 26 and the guide part 27 from the opening 21b of the puncture needle for taking out 21. As a result, the hook 26 and the guide part 27 together move down to near the tip end portion 13b of the suture thread 13 while being extended within the gastric wall 34 and the tip end portion 13b is sandwiched between the hook 26 and the guide part 27 to provide the condition as shown in FIG. 15.

Figure 16:
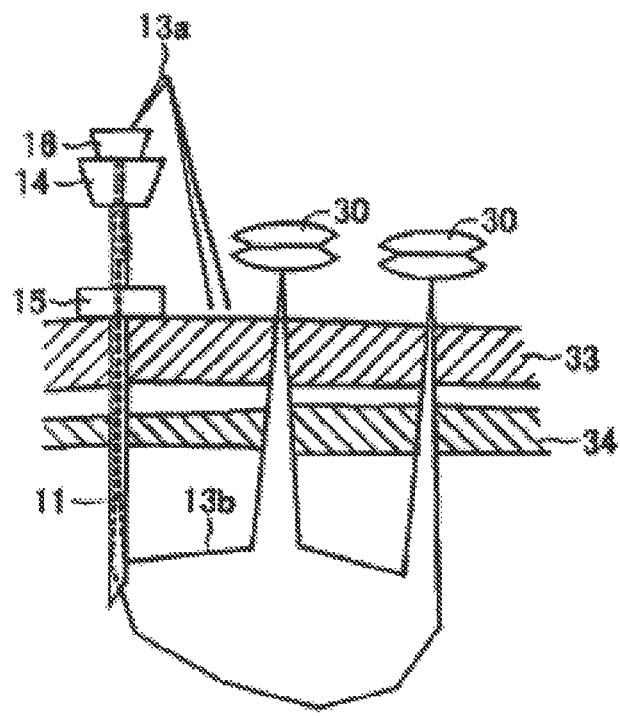
FIG. 16 is a cross sectional view illustrating the suture thread anchored by two anchor members.
Figure 17:
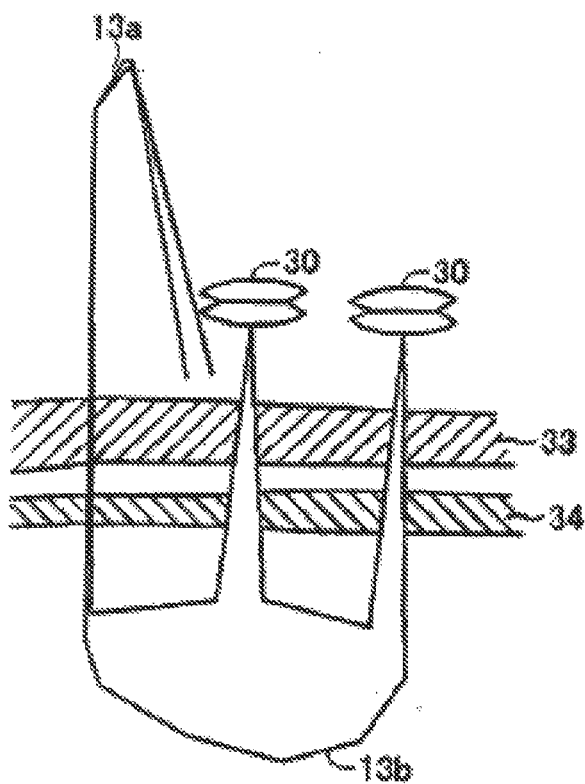
FIG. 17 is a cross sectional view illustrating the puncture needle for insertion pulled out of the stomach.

Next, the grasping part 28 is pulled up to drag the hook 26 engaged with the tip end portion 13b of the suture thread 13 together with the guide part 27 into the inside of the puncture needle for taking out 21 to press the tip end portion 13b of the suture thread 13 against the edge portion of the opening 21b. With this condition, as the thread taking out member 20 is pulled out of the body of the patient, one portion of the tip end portion 13b of the suture thread 13 is passed through the gastric wall 34 and the abdominal wall 33 to protrude from the body of the patient. And, then, the hook 26 is released from the tip end portion 13b of the suture thread 13 and the anchor member 30 is attached thereto to provide the condition as shown in FIG. 16.

Figure 18:
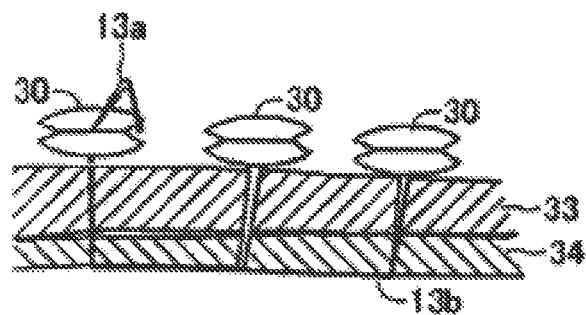
FIG. 18 is a cross sectional view illustrating the condition in which the gastric wall and the abdominal wall is joined by the suture thread and three anchor members.
Figure 19:
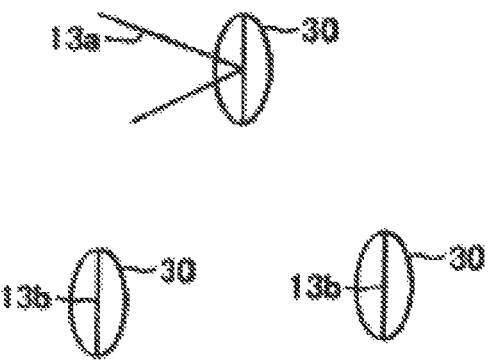
FIG. 19 is a plan view illustrating the sutured site seen from the outside of the patient's body.
Figure 20:
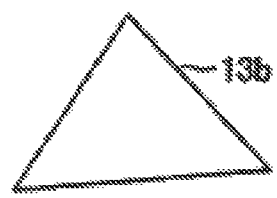
FIG. 20 is a back view illustrating the sutured site seen from the inside of the gastric wall.

Then, the puncture needle for insertion outer tube 11 and the puncture needle for insertion inner tube 12 are pulled out of the body of the patient to protrude the basal end portion 13a of the suture thread 13 from the body of the patient. And, the basal end portion 13a of the suture thread 13 protruding from the body of the patient is pulled out to further draw the basal end portion 13a of the suture thread 13 from the body of the patient by contacting the gastric wall 34 with the abdominal wall 33. In this condition, the basal end portion 13a of the suture thread 13 is wound around the anchor member 30 to tie up both ends of the basal end portion 13a, thereby providing the condition as shown in FIG. 18 and completing the suture. In this case, as the sutured site is seen from the outside of the patient's body, three anchor members 30 engaging with the suture thread 13 are disposed as if they are positioned at each vertex of a triangle as shown in FIG. 19, while as the sutured site is seen from the inside of the gastric, tip end portions 13b of the suture thread 13 are disposed as if they form a triangle.

As described in above, in this suture tool of medical use, one single thread is folded to be a double-suture thread 13 and provides the basal end portion 13a at both ends as well as provides the tip end portion 13b at the folded portion at the center forming a ring. Also, the tip end portion 13b is bended so as to perpendicular to the basal end portion 13a. Accordingly, when the suture thread 13 is passed through the insertion hole 12a of the puncture needle for insertion inner tube 12, the tip end portion 13b is inserted from the guide hole 16a of the hub 16 while being extended into a straight line to protrude from the opening 11b of the puncture needle for insertion outer tube 11, and the tip end portion 13b of the suture thread 13 is protruded from the opening 11b of the puncture needle for insertion outer tube 11, that portion 13b is restored to the original ring shape.

Further, the linear grasping member 22 can be inserted from the guide hole 23a of the hub 23 and the hook 26 and the guide part 27 at the tip end thereof can be protruded from the opening 21b of the puncture needle for taking out 21, and, then, the hook 26 protruded from the opening 21b can be engaged with the tip end portion 13b of the suture thread 13. Therefore, when the puncture needle for taking out 21 together with the linear grasping member 22 is pulled out of the gastric wall 34 and the abdominal wall 33 while the hook 26 is engaged with the tip end portion 13b of the suture thread 13, one portion of the tip end portion 13b of the suture thread 13 is passed through the gastric wall 34 and the abdominal wall 33 to protrude therefrom to the outside.

Therefore, the hook 26 is released from the portion protruded from the abdominal wall 33 to the outside thereof in the tip end portion 13b of the suture thread 13 and the anchor member 30 is engaged with that portion, thereby preventing the one portion of the tip end portion 13b protruded from the abdominal wall 33 to the outside from entering into the inside of the abdominal wall 33. Moreover, in this condition, when the punctured needle for insertion outer tube 11 and the punctured needle for insertion inner tube 12 are pulled out of the gastric wall 34 and the abdominal wall 33, the basal end portion 13a of the suture thread 13 is remained outside of the abdominal wall 33, therefore, that remained portion can be engaged with the anchor member 30 to fix the gastric wall 34 to the abdominal wall 33.

According to this, the operation for engaging the hook 26 with the tip end portion 13b can be easy. Further, the anchor members 30 form slits 31a and 31b extending from the outer periphery of the disc at both sides toward the center, respectively and are provided with stopping holes 32a and 32b formed at the deep end of slits 31a and 31b, respectively. Thus, the suture thread 13 is passed through the slits 31a and 31b, respectively and engaged with the stopping holes 32a and 32b, thereby attaching the anchor members 30 to the suture thread 13. Accordingly, the attachment operation of the anchor members 30 can be simplified as well as the attachment can certainly be made.

Moreover, in the suture tool of medical use described in above, various numbers of the thread taking out members 20 each including the puncture needle for taking out 21 and the linear grasping member 22 may be employed in accordance with the size of a site to be sutured. Therefore, when the organ is fixed at several points, the organ can be fixed to the skin side portion at several points by one operation, whereby the operation for the suture can be simplified and the operation time can be shortened.

Figure 21:
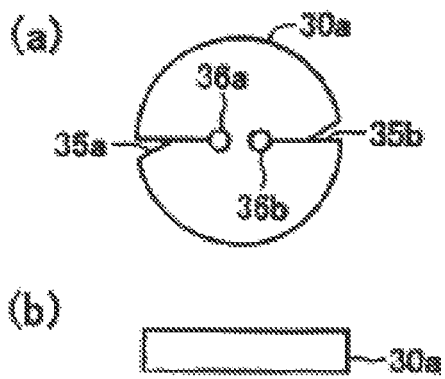
FIG. 21 shows another anchor member; (a) is a plan view and (b) is a side view thereof.

FIG. 21 shows an anchor member 30a included in the suture tool of medical use of another embodiment in accordance with the invention. In the anchor member 30a, stopping holes 36a and 36b each formed at the deeper end portion of slits 35a and 35b, respectively, are provided not at the upper or lower sides of the deeper end of the slits 35a and 35b as shown in FIG. 21(a) but at the deeper end portion of the slits 35a and 35b so as to be in a straight line with the slits 35a and 35b. The other components of anchor member 30a are the same as those of the anchor member 30 as described in above. Similar effect of the embodiment described in above can be achieved by employing this anchor member 30a.

Figure 22:
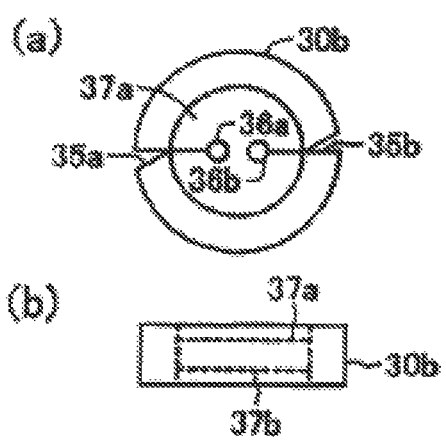
FIG. 22 shows yet another anchor member; (a) is a plan view and (b) is a side view thereof.

FIG. 22 shows an anchor member 30b included in the suture tool of medical use of yet another embodiment in accordance with the invention. In this anchor member 30b, circular recesses 37a and 37b are formed at the front and the back surfaces of the anchor member 30b at the center portion, respectively. The other components of the anchor member 30b are the same as those of the anchor member 30a as described in above. Thus, similar components are represented by similar indications and explanations thereof are omitted. According to this, the anchor member 30b can easily held because of the recesses 37a and 37b to provide an easier operation at the suture. The other effects of the suture tool of medical use including the anchor member 30b are the same as those by the embodiments described in above.

Figure 23:
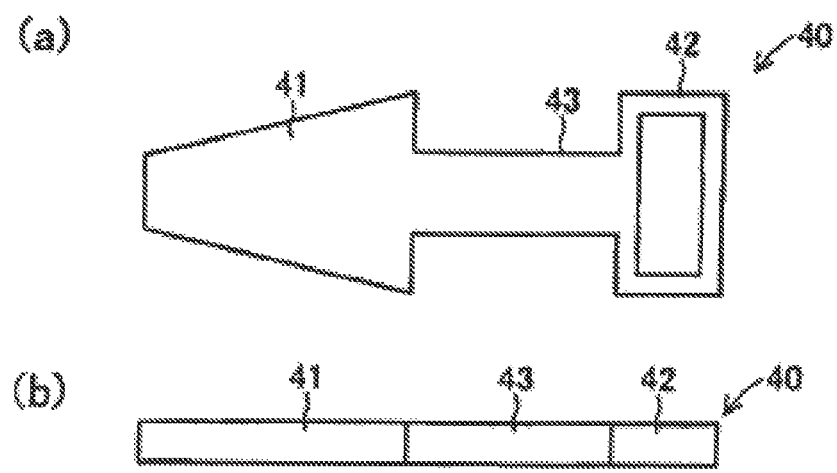
FIG. 23 shows further anchor member(s); (a) is a plan view and (b) is a side view thereof.

FIG. 23 shows an anchor member 40 included in the suture tool of medical use of further embodiment in accordance with the invention. This anchor member 40 is formed into a band made from a resin material of flexibility. That is to say, the anchor member 40 is configured by connecting an engagement portion 41 and an engaged portion 42 by a connecting portion 43, in which The engagement portion 41 is formed into a trapezoid in which the width of the connecting portion 43 side portion is greater than that of the tip end side, while the engaged portion 42 is formed by a rectangular frame. And, the connecting portion 43 is constructed by a narrow long connecting piece. The engaged portion 42 and the connecting portion 43 are capable of being specifically largely deformed, therefore, when the connecting portion 43 is bended and the engagement portion 41 is inserted into the engaged portion 42 of the rectangular frame the engaged portion 42 passes the engagement portion 41 by deforming itself and is restored to the original shape after passing the engagement portion 41 therethrough, thereby preventing the engagement portion 41 from slipping out.

Figure 24:
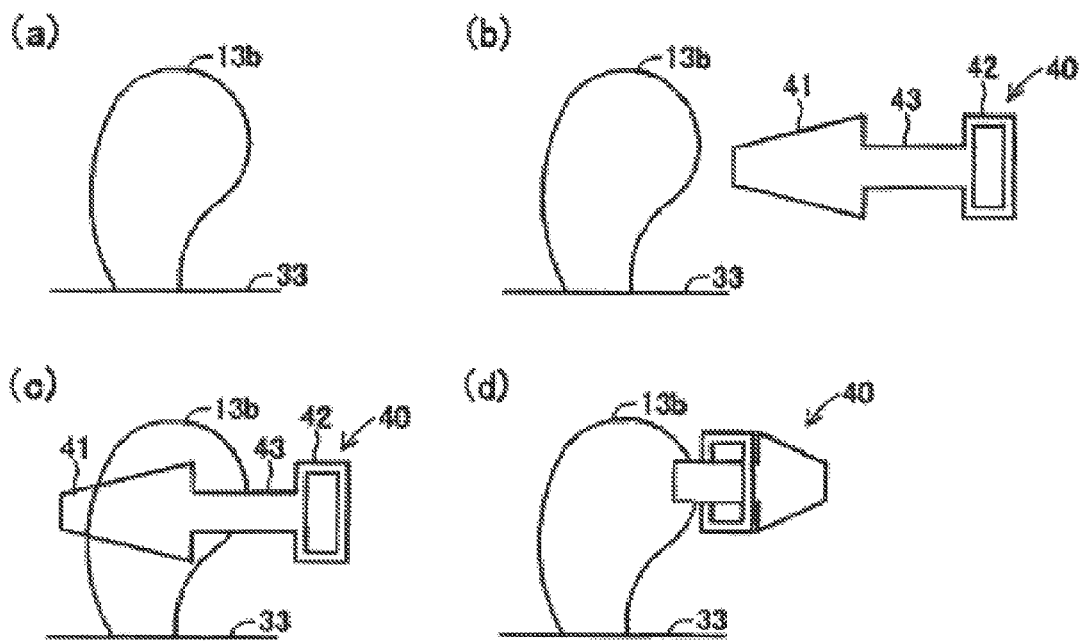
FIG. 24 is an explanation view explaining the condition for mounting the anchor member as shown in FIG. 23 to the suture thread; (a) is the condition in which the suture thread is protruded from the abdominal wall; (b) is the condition in which the anchor member is entering the suture thread; (c) is the condition in which the anchor member is entered within the suture thread; and (d) is the condition in which the anchor member is mounted to the suture thread.

When the anchor member 40 configured in this way is engaged with the tip end portion 13b of the suture thread 13 protruding from the abdominal wall 33 to the outside as shown in FIG. 24(a), firstly, the anchor member 40 is introduced from the engagement portion 41 side into the ring like tip end portion 13b. Then, the anchor member 40 is bended so as to surround the tip end portion 13b as shown in FIG. 24(c) and the engagement portion 41 is inserted into the engaged portion 42 while the connecting portion 43 is aligned with the tip end portion 13b. Accordingly, the engagement portion 41 is maintained in the engagement with the engaged portion 42 and the tip end portion 13b of the suture thread 13 is retained at the outside of the abdominal wall 33. By this configuration, the anchor member 40 can easily be attached to the suture thread 13 as well as the anchor member 40 is difficult to be released from the suture thread 13. The other effects of the suture tool of medical use including the anchor member 30b are the same as those by the embodiments described in above.

Figure 25:
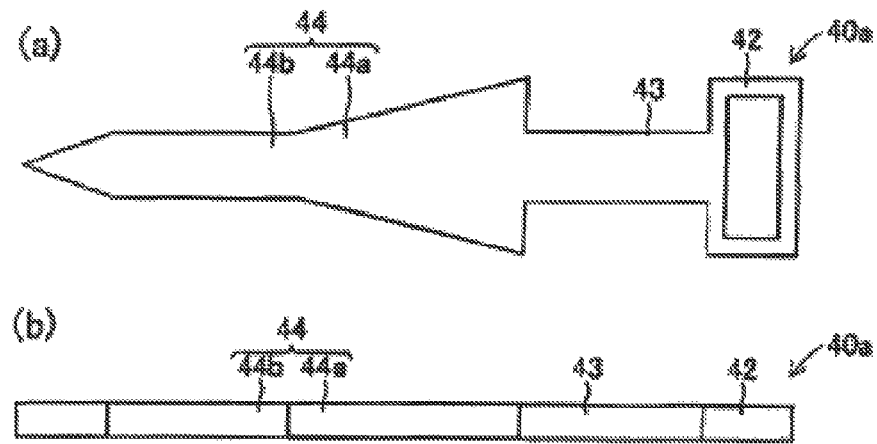
FIG. 25 shows another anchor member; (a) is a plan view and (b) is a side view thereof.

FIG. 25 shows a anchor member 40a included in the suture tool of medical use of yet another embodiment in accordance with the invention. In this anchor member 40a, an engagement portion 44 is provided at a base 44a having the same figure of the engagement portion 41 shown in FIG. 23 and formed into a shape in which a sharp portion 44b is extended. The sharp portion 44b is forwardly extended from the front end portion of the base 44a having the same width of that of the front end portion of the base 44a and, then, tapered to be a sharp end. Therefore, the anchor member 40a can be entered in the tip end portion 13b even though the tip end portion 13b of the suture thread 13 protruded from the abdominal wall 33 is only a little. The other effects of the suture tool of medical use including the anchor member 30b are the same as those by the embodiments described in above.

The suture tool of medical use in accordance with the invention is not intended to limit to the above mentioned embodiments, various modification can be made thereto. For example, in the above described embodiments, though the thread insertion member 10 comprises the puncture needle for insertion outer tube 11 and the puncture needle for insertion inner tube, and the suture thread 13, a cannula made of a resin of an over sleeve substituted by the puncture needle for insertion outer tube 11 and a metallic puncture needle of an inner sleeve capable of being inserted into the cannula may be employed. In this case, the puncture needle is inserted into the cannula to projected the tip end portion of the puncture needle from the cannula and the cannula is penetrated into a site to be sutured together with the puncture needle.

Then, the puncture needle is pulling out while the cannula is retained at the suture site, the puncture needle for insertion inner tube 12 with the suture thread 13 inserted therein is inserted into the cannula and the suture thread 13 is entered into the deeper end of the puncture needle for insertion inner tube 12, whereby the tip end portion 13b of the suture thread 13 can be protruded from the tip end opening of the cannula. Alternatively, the puncture needle for insertion may be comprised only by the puncture needle for insertion outer tube 11 without using the puncture needle for insertion inner tube 12.

Moreover, in the embodiments explained in above, though the tip end portion 13b of the suture thread 13 is shaped into a ring and formed so as to be perpendicular to the base end portion 13a, the tip end portion 13b may be formed such that it extends in the same direction of that of the basal end portion 13a whereby the hook 26 of the linear grasping member 22 can be extended toward the tip end portion 13b of the suture thread 13. Alternatively, the tip end portion 13b of the suture thread 13 and the hook 26 of the linear grasping member 22 may be in any forms so long as they can be engaged with each other.

Also, in the embodiments explained in above, though the suture thread is comprised by single thread, the suture thread 13 may be comprised by a single basal end portion and a ring like tip end portion. Further, in the embodiments explained in above, though the tip end portion 13b of the suture thread 13 pulled out of the body by the puncture needle for taking out 21 and the linear grasping member 22 and the basal end portion 13a of the suture thread 13 protruded from the body as the puncture needle for insertion outer tube 11 and the puncture needle for insertion inner tube 12 are pulled out are anchored by the same anchor members 30, this anchor members may be comprised by different members. For example, the tip end portion 13b of the suture thread 13 is anchored by the anchor members 40, 40a and the like, the basal end portion 13a of the suture thread 13 may be anchored by the anchored members 30, 30a, 30b and the like. Moreover, the suture tool of medical use in accordance with the invention can be used to suture another site within the body, not limited to the suture of the abdominal wall with the gastric wall.

In the suture tool of medical use in accordance with the invention configured in this way, the linear grasping member can be inserted from the basal end opening of the puncture needle for taking out and the tip end portion thereof can be protruded out of the tip end opening. Also, the tip end portion can be engaged with the tip end portion of the suture projecting at the tip end opening of the puncture needle for insertion. Therefore, when the puncture needle for taking out with the linear grasping member is pulled out the organ and the skin side portion while the tip end portion of the linear grasping member is engaged with the tip end portion of the suture, the suture becomes to include a portion located at the outside of the basal end side of the puncture needle for insertion and the inside of the puncture needle for insertion, a portion located at the inside of the organ and a portion protruding to the outside of the skin side portion by passing through the organ and the skin side portion from the inside of the organ.

Accordingly, the linear grasping member is took out of the portion protruding to the outside of the skin side portion in the tip end portion of the suture and that portion is engaged with the anchor member, thereby preventing the tip end portion of the suture protruding to the outside of the skin portion from dragging into the inside of the skin side portion. Also, when the puncture needle for insertion is pulled out of the organ and the skin side portion in this condition, the basal end portion of the suture is remained at the outside of the skin side portion, whereby the organ can be fixed to the skin side portion with the suture and two anchor members by engaging that portion with the anchor members.

The engagement of the tip end portion of the suture and the tip end portion of the linear grasping member in this case can be easily made by applying a property in which the tip end portion of the suture and the tip end portion of the linear grasping member is closed to each other. For example, the tip end portion of the suture is formed so as to extend in lateral direction with an angle generally perpendicular to the basal end portion of the suture when the tip end portion of the suture is protruded from the tip end opening of the puncture needle for insertion, or the tip end portion of the linear grasping member is formed so as to extend in lateral direction with an angle generally perpendicular to the puncture needle for taking out to advance toward the tip end portion of the suture when the tip end portion of the linear grasping member is protruded from the tip end opening of the puncture needle for taking out. The tip end openings or basal end openings of the puncture needle for insertion and the puncture needle for taking out may also be provided not only on the end surface but also on the peripheral surface of the near end surface of the puncture needle for insertion and the puncture needle for taking out.

The tip end portion of the linear grasping member is preferably made of a hook and the like of flexion. Therefore, the engagement of the tip end portion of the suture with the tip end portion of the linear grasping member can certainly made. Also, by configuring the suture and the linear grasping member in this way, the need to curve the tip end portion of the puncture needle for insertion or the puncture needle for taking out can be eliminated, thereby forming the tip end of the puncture needle for insertion or the puncture needle for taking out straight. Accordingly, the penetration of the puncture needle for insertion or the puncture needle for taking out can be easily made. Further, only the portion of the suture protruding from the skin side portion at the basal end portion is needed to be tied up and the other tip end portions of the suture are only required to be hooked to the anchor members, thereby providing easy operation to tie up the suture portions.

For another configurational characteristic of the suture tool of medical use of the invention, the tip end portion of the suture is formed into a ring and the ring can be restored once the tip end portion formed into the ring is stretched into a line as inserted into the puncture needle for insertion and protruded from the tip end opening of the puncture needle for insertion.

In the suture tool of medical use configured in this way, the tip end portion of the suture of being flexible is formed into a ring. And the tip end portion of the ring is inserted from the basal end opening of the puncture needle for insertion and protruded from the tie end opening of the puncture needle for insertion while the tip end portion of the ring is stretched into a line when the suture is passed through the insertion hole of the puncture needle for insertion. Accordingly, the ring of the tip end portion of the suture can be restored after protruding from the tip end opening of the puncture needle for insertion as released from the force stretching the ring into the line. Therefore, the operation for engaging the tip end portion of the linear grasping member with the tip end portion of the suture can easily be performed.

Also, other configurational characteristic of the suture tool of medical use in accordance with the invention is that the tip end portion of the suture is flexuously formed so as to generally perpendicular to the basal end portion of the suture. According to this, since the tip end portion of the ring of the suture is generally perpendicular to the puncture needle for insertion, the tip end portion of the linear grasping member can be positioned near the tip end portion of the suture only by passing through the linear grasping member to be inserted into the puncture needle for taking out once the puncture needle for taking out is penetrated into the patient's body such that the needle is generally parallel to the puncture needle for insertion with the predetermined interval. Therefore, the operation for engaging the tip end of the linear grasping member with the tip end portion of the suture can be further easy.

Another configurational characteristic of the suture tool of medical use in accordance with the invention is that the basal end portion is formed by a double thread from single thread folded into a double thread, as well as, the suture is configured such that the tip end portion thereof is the folded portion of the double thread at the center portion of the single thread. According to this, the forming the suture is simplified because it is needed to process only single thread.

Yet another configurational characteristic of the suture tool of medical use in accordance with the invention is that when the tip end portion of the linear grasping member is engaged with the tip end portion of the suture and the linear grasping member is pulled to the basal end opening side of the puncture needle for taking out, the tip end portion of the suture is engaged with the tip end opening of the puncture needle for taking out and, then, the puncture needle for taking out and the linear grasping member are pulling out of the organ and the skin side portion in this condition and one portion of the tip end portion can be pulled out of the outside of the skin side portion. According to this, the size of the puncture needle for taking out can be increased since the need to pass the tip end portion of the suture into the puncture needle for taking out can be eliminated, thereby smoothly performing the puncture of the puncture needle for taking out.

Further configurational characteristic of the suture tool of medical use in accordance with the invention, multiple numbers of the puncture needles for taking out, the linear grasping members and the anchor members are provided, respectively. According to this, the multiple number of the tip end portions of rings of the suture inserted into the patient's body through the puncture needle for insertion can be engaged with the tip end portions of the linear grasping members inserted through the multiple numbers of the puncture needles for taking out, respectively, positioned with the predetermined spaces and protruded out of the patient's body. Therefore, an organ required to fix to the skin side portion at several portions such as big organ can be fixed by one suture treatment. As a result, the treatment for suture can be simplified, as well as, the operation time can be shortened.

And another configurational characteristic of the suture tool of medical use in accordance with the invention is that the anchor members are provided with a notch part where the suture can be engaged, the notch part is formed at least one location in the outer peripheral portion of a plate like body. In this case, the plate like body comprising the anchor member may be in any shape such as circular, rectangular, triangular shapes and it is preferred to provide the number or shape of the notch part corresponding to the shape of the plate like body. For example, when the plate like body is circular or rectangular shape, it is preferred that notch parts are provided at both ends spaced apart from each other by 180 degrees in the plate like body. According to this, the suture can be engaged with the anchor member by winding the tip end portion of the suture protruded about the notch part provided in the anchor member, thereby simplifying the operation for the engagement. Furthermore, the notch part may be provided by forming the anchor member into a shape of star or three rhombuses.

Yet another configurational characteristic of the suture tool of medical use in accordance with the invention is that the anchor member is configured in a band like member which is capable of being mounted while being wound around the suture. In this case, the band like member is formed by a flexible resin and there is a band being capable of deforming into a ring. Again, according to this, the tip end portion of the suture protruding to the outside of the skin side portion can be prevented from dragging in the inside of the skin side portion.

Further, other configurational characteristic of the suture tool of medical use in accordance with the invention is that the anchor member comprises a stopper for stopping the tip end portion of the suture to be pulled out of the outside of the skin side portion by pulling out the puncture needle for taking out and the linear grasping member out of the organ and the skin side portion, and a stopper for stopping the basal end portion of the suture protruding to the outside of the skin side portion when the puncture needle for insertion is pulled out of the organ and the skin side portion.

In this case, two anchor members may be of the same shape or different shapes. When anchor members are formed by different shapes, it is preferred that the anchor member to be engaged with the tip end portion of the suture is configured by a shape to which the suture can readily hooked, while the anchor member to be engaged with the basal end portion of the suture is configured by a shape where the suture can easily be tied up while being wound the anchor member.

What is claimed is:

1. A suture tool comprising:
   a first puncture needle for inserting a suture in a patient, said first puncture needle having an insertion hole and a hub having a guide hole at a basal end of the first puncture needle;
   a suture sized and shaped for insertion into the insertion hole of said first puncture needle for inserting the suture in the patient, said suture having a tip end portion;
   a second puncture needle for taking out sutures from the patient, said second puncture needle having an insertion hole;
   a linear grasping member sized and shaped for insertion into said insertion hole of said second puncture needle for removing the suture from the patient, the grasping member having an elongate intra needle and a hook extending obliquely from the intra needle, the hook of said linear grasping member being engageable with a tip end portion of the suture; and
   a plug removably insertable into the guide hole of the hub to fix the suture in the insertion hole of said first puncture needle.

2. The suture tool in accordance with claim 1, wherein said tip end portion of the suture comprises a ring.

3. The suture tool in accordance with claim 2, wherein said tip end portion of said suture is perpendicular to a basal end portion of said suture.

4. The suture tool in accordance with claim 3, wherein said basal end portion of said suture comprises a double thread and said suture is configured such that said tip end portion of said suture comprises a folded portion of the double thread.

5. The suture tool in accordance with claim 1, wherein said hook of said linear grasping member is engaged with said tip end portion of said suture, said linear grasping member is pulled to a basal end opening side of said second puncture needle, and said tip end portion of said suture is engaged with a tip end opening of said second puncture needle when taking out sutures.

6. The suture tool in accordance with claim 1, wherein said suture tool comprises a plurality of said second puncture needles and a plurality of said linear grasping members.

7. The suture tool in accordance with claim 1, further comprising an anchor member including a plate having a notch part located in at least one location in an outer peripheral portion of the plate, a slit extending from the notch part toward a center of the plate, and an opening at an end of the slit near the center of the plate.

8. The suture tool in accordance with claim 1, further comprising an anchor member including a band.

9. The suture tool in accordance with claim 1, further comprising an anchor member including a stopper.

10. The suture tool in accordance with claim 1, wherein said linear grasping member is inserted into said second puncture needle for taking out sutures from a basal end opening of the insertion hole of said second puncture needle.

11. The suture tool in accordance with claim 7, further comprising a second notch part in the outer peripheral portion of the plate, a second slit extending from the second notch part toward the center of the plate, and a second opening at an end of the second slit near the center of the plate.

* * * * *